US009029642B2

(12) United States Patent
Croughan

(10) Patent No.: US 9,029,642 B2
(45) Date of Patent: May 12, 2015

(54) HERBICIDE RESISTANT RICE

(75) Inventor: Timothy P. Croughan, Crowley, LA (US)

(73) Assignee: Board of Supervisors of Louisiana State University And Agricultural and Mechanical College, Baton Rouge, LA (US)

(*) Notice: Subject to any disclaimer, the term of this patent is extended or adjusted under 35 U.S.C. 154(b) by 0 days.

(21) Appl. No.: 12/819,360

(22) Filed: Jun. 21, 2010

(65) Prior Publication Data

US 2010/0257623 A1 Oct. 7, 2010

Related U.S. Application Data

(63) Continuation of application No. 12/050,448, filed on Mar. 18, 2008, now Pat. No. 7,754,947, which is a continuation of application No. 09/934,973, filed on Aug. 22, 2001, now Pat. No. 7,345,221, which is a continuation of application No. 09/830,194, filed as application No. PCT/US99/26062 on Nov. 5, 1999, now Pat. No. 7,019,196.

(60) Provisional application No. 60/107,255, filed on Nov. 5, 1998.

(51) Int. Cl.
*A01H 5/10* (2006.01)

(52) U.S. Cl.
CPC ........................................ *A01H 5/10* (2013.01)

(58) Field of Classification Search
None
See application file for complete search history.

(56) References Cited

U.S. PATENT DOCUMENTS

| 4,443,971 | A |   | 4/1984  | Chaleff ............................. 47/58 |
|-----------|---|---|---------|---------------------------------------------|
| 4,761,373 | A |   | 8/1988  | Anderson et al. .......... 435/172.3         |
| 4,774,381 | A |   | 9/1988  | Chaleff et al. ..................... 800/1   |
| 5,013,659 | A |   | 5/1991  | Bedbrook et al. .......... 435/172.3         |
| 5,084,082 | A |   | 1/1992  | Sebastian .......................... 71/90   |
| 5,304,732 | A |   | 4/1994  | Anderson et al. ............. 800/235        |
| 5,331,107 | A |   | 7/1994  | Anderson et al. ............. 800/235        |
| 5,545,822 | A | * | 8/1996  | Croughan ...................... 800/300      |
| 5,605,011 | A |   | 2/1997  | Bedbrook et al. ................ 47/58       |
| 5,633,437 | A |   | 5/1997  | Bernasconi et al. .......... 800/205         |
| RE35,661  | E |   | 11/1997 | Thill ............................. 800/200  |
| 5,718,079 | A |   | 2/1998  | Anderson et al. ................ 47/58       |
| 5,731,180 | A |   | 3/1998  | Dietrich ...................... 435/172.3    |
| 5,736,629 | A |   | 4/1998  | Croughan ..................... 800/235       |
| 5,767,361 | A |   | 6/1998  | Dietrich ........................ 800/205    |
| 5,767,366 | A |   | 6/1998  | Sathasivan et al. ........... 800/205        |
| 5,773,702 | A |   | 6/1998  | Penner et al. ................. 800/230      |
| 5,773,703 | A |   | 6/1998  | Croughan ..................... 800/235       |
| 5,773,704 | A |   | 6/1998  | Croughan ..................... 800/235       |
| 5,853,973 | A |   | 12/1998 | Kakefuda et al. ................ 435/4       |
| 5,859,348 | A |   | 1/1999  | Penner et al. ................. 800/230      |
| 5,928,937 | A |   | 7/1999  | Kakefuda et al. .......... 435/320.1         |
| 5,952,553 | A |   | 9/1999  | Croughan ................. 800/320.2         |
| 6,211,438 | B1 |   | 4/2001 | Anderson et al. ............. 800/300        |
| 6,211,439 | B1 |   | 4/2001 | Anderson et al. ............. 800/300        |
| 6,222,100 | B1 |   | 4/2001 | Anderson et al. ............. 800/300        |
| 6,274,796 | B1 |   | 8/2001 | Croughan ................. 800/320.2         |
| 6,943,280 | B2 | * | 9/2005 | Croughan ..................... 800/300       |
| 7,019,196 | B1 | * | 3/2006 | Croughan ..................... 800/300       |
| 7,345,221 | B2 | * | 3/2008 | Croughan ..................... 800/300       |
| 7,399,905 | B2 | * | 7/2008 | Croughan ..................... 800/300       |
| 7,495,153 | B2 | * | 2/2009 | Croughan ..................... 800/300       |
| 7,754,947 | B2 | * | 7/2010 | Croughan ..................... 800/300       |
| 2008/0167186 | A1 |   | 7/2008 | Croughan ................... 800/300      |
| 2009/0025108 | A1 |   | 1/2009 | Croughan ................... 800/300      |

FOREIGN PATENT DOCUMENTS

| EP | 0 257 993    | 3/1988  |   |
|----|--------------|---------|---|
| EP | 0 364 580    | 4/1990  |   |
| EP | 0 525 384    | 2/1993  |   |
| EP | 0 154 204    | 1/1994  |   |
| EP | 0 730 030    | 9/1996  |   |
| EP | 0 965 265    | 12/1999 |   |
| WO | WO 90/14000  | 11/1990 |   |
| WO | WO 92/08794  | 5/1992  | * |
| WO | WO 96/33270  | 10/1996 |   |
| WO | WO 97/41218  | 11/1997 |   |
| WO | WO 98/02526  | 1/1998  |   |
| WO | WO 98/02527  | 1/1998  |   |
| WO | WO 00/26390  | 5/2000  |   |
| WO | WO 00/27182  | 5/2000  |   |
| WO | WO 01/65922  | 9/2001  |   |
| WO | WO 01/82685  | 11/2001 |   |
| WO | WO 01/85970  | 11/2001 |   |

OTHER PUBLICATIONS

Tranel and Wright 2002, Weed Science 50: 700-712.*
Affidavit of Steven D. Linscombe (Nov. 8, 2004).
Barrett, "Herbicides and Their Mechanisms of Action," eds. Cobb and Kirkwood, CRC Press, Boca Raton, FL, pp. 25-35 (2000).
Bernasconi et al., J. Biological Chemistry, vol. 270, No. 29, pp. 17381-17385 (1995).
Croughan, T. et al., "Applications of Biotechnology to Rice Improvement," *Proc. 25th Rice Tech. Work. Groups*, pp. 62-63 (1994).
Croughan, T., "Application of Tissue Culture Techniques to the Development of Herbicide Resistant Rice," *Louisiana Agriculture*, vol. 37, No. 3, pp. 25-26 (1994).
Croughan, T. et al., "Imidazolidone-Resistant Rice," 90th Annual Research Report, Rice Research Station, 1998, p. 511 (Dec. 1999).
Croughan, T. et al., "Assessment of Imidazolidone-Resistant Rice," *87th Annual Research Report, Rice Research Station*, 1995, pp. 491-525 (Sep. 1996).
Croughan, T., "Herbicide Resistant Rice," *Proc. 25th Rice Tech. Work. Groups*, p. 44 (1994).
Croughan, T. et al., "Rice Biotechnology Research," 89th Annual Research Report, Rice Research Station, 1997, p. 464 (Sep. 1998).
Croughan, T. et al., "IMI-Rice Evaluations," 88th Annual Research Report, Rice Research Station, 1996, pp. 603-629 (Sep. 1997).

(Continued)

*Primary Examiner* — David H Kruse
(74) *Attorney, Agent, or Firm* — John H. Runnels

(57) ABSTRACT

Rice plants are disclosed with multiple sources of resistance to herbicides that normally inhibit a plant's acetohydroxyacid synthase (AHAS) enzyme. Besides controlling red rice, many AHAS-inhibiting herbicides also effectively control other weeds that are common in rice fields. Several of these herbicides have residual activity, so that one treatment can control both existing weeds and weeds that sprout later. With effective residual activity against red rice and other weeds, rice producers now have a weed control system superior to those that are currently available commercially.

28 Claims, No Drawings

(56) References Cited

OTHER PUBLICATIONS

Croughan, T., "Improvement of Lysine Content and Herbicide Resistance in Rice Through Biotechnology," USDA CRIS Report Accession No. 0168634 (for Fiscal Year 1997—actual publication date currently unknown).

Croughan, T., "Improvement of Lysine Content and Herbicide Resistance in Rice Through Biotechnology," USDA CRIS Report Accession No. 0168634 (for Fiscal Year 1999—actual publication date currently unknown).

Croughan, T., "Improvement of Lysine Content and Herbicide Resistance in Rice Through Biotechnology," USDA CRIS Report Accession No. 0168634 (for Fiscal Year 2000—actual publication date currently unknown).

Croughan, T., "Production of Rice Resistant to AHAS—Inhibiting Herbicides," Congress on Cell and Tissue Culture, Tissue Culture Association, In Vitro, vol. 30A, p. 60, Abstract P-1009 (Jun. 4-7, 1994).

Croughan, T. et al., "Rice and Wheat Improvement through Biotechnology," *84th Annual Research Report, Rice Research Station*, 1992, pp. 100-103 (1993).

Croughan, T. et al., "Rice and Wheat Improvement through Biotechnology," *85th Annual Research Report, Rice Research Station*, 1993, pp. 116-156 (1994).

Croughan, T. et al., "Rice and Wheat Improvement through Biotechnology," USDA CRIS Report Accession No. 0150120 (for Fiscal Year 1994—actual publication date currently unknown).

Croughan, T. et al., "Rice Improvement through Biotechnology," *86th Annual Research Report, Rice Research Station*, 1994, pp. 461-482 (Sep. 1995).

Duggleby, R., "Identification of an Acetolactate Synthase Small Subunit Gene in Two Eukaryotes," Gene, vol. 190, pp. 245-249 (1997).

"DuPont™ Londax® Herbicide," Section 3 Specimen Label No. H-64161, available on Mar. 4, 2003 from http://www.dupont.com/ag/labelmsds_search.html (2001).

Hattori et al., Molecular and General Genetics, vol. 232, pp. 67-173 (1992).

Hipple, L. et al., "AHAS Characterization of Imidazolinone Resistant Rice," pp. 68-69 in Proceedings of the 27th Rice Technical Working Group Meeting (1999).

Hipple, L. et al., "AHAS Characterization of Imidazolinone Resistant Rice," pp. 45-46 in Program of the 27th Rice Technical Working Group Meeting (Mar. 1998).

Lee et al., "The Molecular Basis of Sulfonylurea Herbicide Resistance in Tobacco," The EMBO J., vol. 7, No. 5, pp. 1241-1248 (1988).

Mazur et al., "Isolation and Characterization of Plant Genes Coding for Acetolactate Synthase, the Target Enzyme for Two Classes of Herbicides," Plant Physiol., vol. 85, pp. 1110-1117 (1987).

Miki et al., "Transformation of *Brassica napus* canola cultivars with *Arabidopsis thaliana* Acetohydroxyacid Synthase Genes and Analysis of Herbicide Resistance," Theor. Appl. Genet., vol. 80, pp. 449-458 (1990).

Newhouse et al., "Mutations in corn (*Zea mays* L.) Conferring Resistance to Imidazolinone Herbicides," Theor. Appl. Genet., vol. 83, pp. 65-70 (1991).

Odell et al., "Comparison of Increased Expression of Wild-Type and Herbicide-Resistant Acetolactate Synthase Genes in Transgenic Plants, and Indication of Postranscriptional Limitation on Enzyme Activity," Plant Physiol., vol. 94, pp. 1647-1654 (1990).

Reek, G. Et al., "'Homology' in Proteins and Nucleic Acids: A Terminology Muddle and a Way out of it," Cell, vol. 50, p. 667 (1987).

Rice, W. et al., "Delayed Flood for Rice Water Weevil Control using Herbicide Resistant Germplasm," p. 134 in Proceedings of the 27th Rice Technical Working Group Meeting (1999).

Rice, W. et al., "Delayed flood for management of rice water weevil (Coleopterae: Curculionidae)," Environmental Entomology, vol. 28, No. 6, pp. 1130-1135 (Dec. 1999).

Rice, W. et al., "Delayed Flood for Rice Water Weevil Control using Herbicide Resistant Germplasm," p. 61 in Program of the 27th Rice Technical Working Group Meeting (Mar. 1998).

Sathasivan et al., "Molecular Basis of Imidazolinone Herbicide Resistance in *Arabidopsis thaliana* var Columbia," Plant Physiol. vol. 97, pp. 1044-1050 (1991).

Sathasivan et al., "Nucleotide Sequence of a Mutant Acetolactate Synthase Gene from an Imidazolinone-resistant *Arabidopsis thaliana* var. Columbia," Nucleic Acids Research vol. 18, No. 8, p. 2188 (1990).

Saxena et al., "Herbicide Resistance in *Datura innoxia*," Plant Physiol., vol. 86, pp. 863-867 (1988).

Sebastian et al., "Soybean Mutants with Increased Tolerance for Sulfonylurea Herbicides," Crop. Sci., vol. 27, pp. 948-952 (1987).

Shimamoto et al., "Fertile Transgenic Rice Plants Regenerated from Transformed Protoplasts," Nature, vol. 338, pp. 274-276 (1989).

Singh, B.K. et al., "Assay of Acetohydroxyacid Synthase," *Analytical Biochemistry*, vol. 171, pp. 173-179 (1988).

Terakawa et al., "Rice Mutant Resistant to the Herbicide Bensulfuron Methyl (BSM) by in vitro Selection," Japan. J. Breed., vol. 42, pp. 267-275 (1992).

Webster, E. et al., "Weed Control Systems for Imidazolinone-Rice," p. 215 in Proceedings of the 27th Rice Technical Working Group Meeting (1999).

Webster, E. et al., "Weed Control Systems for Imi-Rice," p. 33 in Program of the 27th Rice Technical Working Group Meeting (Mar. 1998).

Wiersma et al., "Isolation, Expression and Phylogenetic Inheritance of an Acetolactate Synthase Gene from *Brassica napus*," Mol. Gen. Genet., vol. 219, pp. 413-420 (1989).

Chang, A.K. et al., "Herbicide-resistant Forms of *Arabidopsis thaliana* Acetohydroxyacid Synthase: Characterization of the Catalytic Properties and Sensitivity to Inhibitors of Four Defined Mutants," Biochem. J., vol. 333, pp. 765-777 (1998).

Lee, Y-T et al., "Effect of Mutagenesis at Serine 653 of *Arabidopsis thaliana* Acetohydroxyacid Synthase on the Sensitivity to Imidazolinone and Sulfonylurea Herbicides," FEBS Letters, vol. 452, pp. 341-345 (1999).

Shaner D. et al., "Imidazolinone-Resistant Crops: Selection, Characterization and Management," *Herbicide-Resistant Crops: Agricultural, Environmental, Economic, Regulatory, and Technical Aspects*, Lewis Publishers, pp. 144-157 (1996).

* cited by examiner

HERBICIDE RESISTANT RICE

This is a continuation of patent application Ser. No. 12/050,448, filed Mar. 18, 2008, now allowed with the issue fee paid; which was a continuation of patent application Ser. No. 09/934,973, filed Aug. 22, 2001, now U.S. Pat. No. 7,345,221; which was a continuation of patent application Ser. No. 09/830,194, 35 U.S.C. §371 date Apr. 23, 2001, now U.S. Pat. No. 7,019,196; which was the United States national stage of international patent application PCT/US1999/026062, filed Nov. 5, 1999; which claimed the benefit of the Nov. 5, 1998 filing date of U.S. provisional patent application Ser. No. 60/107,255 under 35 U.S.C. §119(e); the complete disclosures of all of which are hereby incorporated by reference.

TECHNICAL FIELD

This invention pertains to herbicide resistant rice, particularly to rice resistant to herbicides that normally interfere with the plant enzyme acetohydroxyacid synthase (AHAS), such as imidazolinone herbicides and sulfonylurea herbicides.

BACKGROUND ART

The development of novel herbicide resistance in plants offers significant production and economic advantages. Rice production is frequently restricted by the prevalence of a weedy relative of rice that flourishes in commercial rice fields. The weed is commonly called "red rice," and belongs to the same species as cultivated rice (*Oryza sativa* L.). The genetic similarity of red rice and commercial rice has made herbicidal control of red rice difficult. The herbicides Ordram™ (molinate: S-ethyl hexahydro-1-H-azepine-1-carbothioate) and Bolero™ (thiobencarb: S-[(4-chlorophenyl)methyl]diethylcarbamothioate) offer partial suppression of red rice, but no herbicide that actually controls red rice is currently used in commercial rice fields because of the simultaneous sensitivity of existing commercial cultivars of rice to such herbicides. The development of mutant commercial rice lines resistant to herbicides that are effective on red rice will greatly increase the ability to control red rice infestations.

Rice producers in the southern United States typically rotate rice crops with soybeans to help control red rice infestations. While this rotation is not usually desirable economically, it is frequently necessary because no herbicide is currently available to control red rice infestations selectively in commercial rice crops. During the soybean rotation, the producer has a broad range of available herbicides that may be used on red rice, so that rice may again be grown the following year. United States rice producers can lose $200-$300 per acre per year growing soybeans instead of rice, a potential loss affecting about 2.5 million acres annually. Additional losses in the United States estimated at $50 million per year result from the lower price paid by mills for grain shipments contaminated with red rice. Total economic losses due to red rice in southern United States rice production are estimated to be $500 to $750 million a year. Economic losses due to red rice are even greater in other rice producing countries.

Rice producers typically use the herbicides propanil (trade name Stam™) or molinate (trade name Ordram™) to control weeds in rice production. Propanil has no residual activity. Molinate is toxic to fish. Neither of these herbicides controls red rice. Imazethapyr ((±)-2-[4,5-dihydro-4-methyl-4-(1-methylethyl)-5-oxo-1H-imidazol-2-yl]-5-ethyl-3-pyridinecarboxylic acid) offers an environmentally acceptable alternative to molinate, has the residual weed control activity that propanil lacks, and is a very effective herbicide on red rice. Imazethapyr also offers excellent control of other weeds important in rice production, including barnyardgrass. Barnyardgrass is a major weed in rice production, and is currently controlled with propanil or molinate. However, there are reports that barnyardgrass is developing resistance to propanil.

The total potential market for rice varieties that are resistant to a herbicide that can control red rice is about 5.3 million acres in the United States, and the potential market outside the United States is much larger. World rice production occupies about 350 million acres. Red rice is a weed pest in rice production in the United States, Brazil, Australia, Spain, Italy, North Korea, South Korea, Philippines, Vietnam, China, Brazil, Argentina, Colombia, India, Pakistan, Bangladesh, Japan, Ecuador, Mexico, Cuba, Malaysia, Thailand, Indonesia, Sri Lanka, Venezuela, Myanmar, Nigeria, Uruguay, Peru, and in other rice-producing countries.

Herbicides that inhibit the enzyme acetohydroxyacid synthase would offer a number of advantages over currently available herbicides if they could be used in commercial rice production. Potential advantages include long residual activity against weeds, effective control of the more important weeds in rice production, including red rice, and relative environmental acceptability. Even in regions where red rice is not currently a problem, the availability of herbicide-resistant rice can have a major influence on rice production practices by providing the farmer with a new arsenal of herbicides suitable for use in rice fields.

U.S. Pat. No. 4,761,373 describes the development of mutant herbicide-resistant maize plants through exposing tissue cultures to herbicide. The mutant maize plants were said to have an altered enzyme, namely acetohydroxyacid synthase, that conferred resistance to certain imidazolinone and sulfonamide herbicides. See also U.S. Pat. Nos. 5,304,732, 5,331,107, and 5,718,079; and European Patent Application 0 154 204 A2.

Lee et al., "The Molecular Basis of Sulfonylurea Herbicide Resistance in Tobacco," *The EMBO J.*, vol. 7, no. 5, pp. 1241-1248 (1988), describe the isolation and characterization from *Nicotiana tabacum* of mutant genes specifying herbicide resistant forms of acetolactate synthase (also known as acetohydroxyacid synthase), and the reintroduction of those genes into sensitive lines of tobacco.

Saxena et al., "Herbicide Resistance in *Datura innoxia*," *Plant Physiol.*, vol. 86, pp. 863-867 (1988) describe several *Datura innoxia* lines resistant to sulfonylurea herbicides, some of which were also found to be cross-resistant to imidazolinone herbicides.

Mazur et al., "Isolation and Characterization of Plant Genes Coding for Acetolactate Synthase, the Target Enzyme for Two Classes of Herbicides," *Plant Physiol.* vol. 85, pp. 1110-1117 (1987), discuss investigations into the degree of homology among acetolactate synthases from different species.

U.S. Pat. No. 5,767,366 discloses transformed plants with genetically engineered imidazolinone resistance, conferred through a gene cloned from a plant such as a mutated *Arabidopsis thaliana*. See also a related paper, Sathasivan et al., "Nucleotide Sequence of a Mutant Acetolactate Synthase Gene from an Imidazolinone-resistant *Arabidopsis thaliana* var. *Columbia*," *Nucleic Acids Research* vol. 18, no. 8, p. 2188 (1990).

Examples of herbicide-resistant AHAS enzymes in plants other than rice are disclosed in U.S. Pat. No. 5,013,659; K. Newhouse et al., "Mutations in corn (*Zea mays* L.) Conferring Resistance to Imidazolinone Herbicides," *Theor. Appl. Genet.*, vol. 83, pp. 65-70 (1991); K. Sathasivan et al., "Molecular Basis of Imidazolinone Herbicide Resistance in *Arabidopsis thaliana* var *Columbia,*" *Plant Physiol.* vol. 97, pp. 1044-1050 (1991); B. Miki et al., "Transformation of *Brassica napus* canola cultivars with *Arabidopsis thaliana* Acetohydroxyacid Synthase Genes and Analysis of Herbicide Resistance," *Theor. Appl. Genet., vol.* 80, pp. 449-458 (1990); P. Wiersma et al., "Isolation, Expression and Phylogenetic Inheritance of an Acetolactate Synthase Gene from *Brassica napus,*" *Mol. Gen. Genet.,* vol. 219, pp. 413-420 (1989); and J. Odell et al., "Comparison of Increased Expression of Wild-Type and Herbicide-Resistant Acetolactate Synthase Genes in Transgenic Plants, and Indication of Postranscriptional Limitation on Enzyme Activity," *Plant Physiol., vol.* 94, pp. 1647-1654 (1990).

S. Sebastian et al., "Soybean Mutants with Increased Tolerance for Sulfonylurea Herbicides," *Crop. Sci., vol.* 27, pp. 948-952 (1987) discloses soybean mutants resistant to sulfonylurea herbicides. See also U.S. Pat. No. 5,084,082.

K. Shimamoto et al., "Fertile Transgenic Rice Plants Regenerated from Transformed Protoplasts," *Nature, vol.* 338, pp. 274-276 (1989) discloses a genetic transformation protocol in which electroporation of protoplasts was used to transform a gene encoding β-glucuronidase into rice.

T. Terakawa et al., "Rice Mutant Resistant to the Herbicide Bensulfuron Methyl (BSM) by in vitro Selection," *Japan. J. Breed., vol.* 42, pp. 267-275 (1992) discloses a rice mutant resistant to a sulfonylurea herbicide, derived by selective pressure on callus tissue culture. Resistance was attributed to a mutant AHAS enzyme.

Following are publications by the inventor (or the inventor and other authors) concerning research on herbicide-resistant rice varieties. These publications are T. Croughan et al., "Rice and Wheat Improvement through Biotechnology," 84*th Annual Research Report, Rice Research Station,* 1992, pp. 100-103 (1993); T. Croughan et al., "Rice and Wheat Improvement through Biotechnology," 85*th Annual Research Report, Rice Research Station,* 1993, pp. 116-156 (1994); T. Croughan, "Application of Tissue Culture Techniques to the Development of Herbicide Resistant Rice," *Louisiana Agriculture, vol.* 37, no. 3, pp. 25-26 (1994); T. Croughan et al., "Rice Improvement through Biotechnology," 86*th Annual Research Report, Rice Research Station,* 1994, pp. 461-482 (1995); T. Croughan et al., "Assessment of Imidazolinone-Resistant Rice," 87*th Annual Research Report, Rice Research Station,* 1994, pp. 491-525 (September 1996); T. Croughan et al., "IMI-Rice Evaluations," 88*th Annual Research Report, Rice Research Station,* 1996, pp. 603-629 (September 1997); T. Croughan et al., "Imidazolinone-Resistant Rice," 89*th Annual Research Report, Rice Research Station,* 1997, p. 464 (September 1998); T. Croughan et al., "Rice and Wheat Improvement through Biotechnology," USDA CRIS Report Accession No. 0150120 (for Fiscal Year 1994-actual publication date currently unknown); T. Croughan et al., "Improvement of Lysine Content and Herbicide Resistance in Rice through Biotechnology," USDA CRIS Report Accession No. 0168634 (for Fiscal Year 1997-actual publication date currently unknown); T. Croughan, "Herbicide Resistant Rice," *Proc.* 25*th Rice Tech. Work. Groups,* p. 44 (1994); T. Croughan et al., "Applications of Biotechnology to Rice Improvement," *Proc.* 25*th Rice Tech. Work. Groups,* pp. 62-63 (1994); T. Croughan, "Production of Rice Resistant to AHAS-Inhibiting Herbicides," Congress on Cell and Tissue Culture, Tissue Culture Association, In Vitro, vol. 30A, p. 60, Abstract P-1009 (Jun. 4-7, 1994). (Note that the Annual Research Reports of the Rice Research Station are published in the year after the calendar year for which activities are reported. For example, the 84*th Annual Research Report, Rice Research Station,* 1992, summarizing research conducted in 1992, was published in 1993.) The reports in the 87*th* and 88*th Annual Research Report, Rice Research Station* (published September 1996 and September 1997, respectively) mention the breeding line 93AS3510 in tables giving data on certain herbicide resistance trials. These reports gave no information on how the breeding line was developed. The breeding line was not publicly available at the times these reports were published. The breeding line 93AS3510 is the same as the ATCC 97523 rice that is described in greater detail in the present inventor's later-published international application WO 97/41218 (1997) and U.S. Pat. Nos. 5,736, 629, 5,773,704, 5,952,553, and 6,274,796.

See also E. Webster et al., "Weed Control Systems for Imi-Rice," p. 33 in *Program of the* 27*th Rice Technical Working Group Meeting* (March 1998); L. Hipple et al., "AHAS Characterization of Imidazolinone Resistant Rice," pp. 45-46 in *Program of the* 27*th Rice Technical Working Group Meeting* (March 1998); W. Rice et al., "Delayed Flood for Rice Water Weevil Control using Herbicide Resistant Germplasm," p. 61 in *Program of the* 27*th Rice Technical Working Group Meeting* (March 1998); E. Webster et al., "Weed Control Systems for Imidazolinone-Rice," p. 215 in *Proceedings of the* 27*th Rice Technical Working Group Meeting* (1999); L. Hipple et al., "AHAS Characterization of Imidazolinone Resistant Rice," pp. 68-69 in *Proceedings of the* 27*th Rice Technical Working Group Meeting* (1999); and W. Rice et al., "Delayed Flood for Rice Water Weevil Control using Herbicide Resistant Germplasm," p. 134 in *Proceedings of the* 27*th Rice Technical Working Group Meeting* (1999).

The present inventor's U.S. Pat. No. 5,545,822 discloses a line of rice plants having a metabolically-based resistance to herbicides that interfere with the plant enzyme acetohydroxyacid synthase; i.e., the herbicide resistance of these rice plants was not due to a resistant AHAS enzyme. (See published international application WO 97/41218, pages 6-9.) See also the present inventor's U.S. Pat. No. 5,773,703.

The present inventor's published international application WO 97/41218 discloses one line of rice plants having a mutant AHAS enzyme that is resistant to herbicides that interfere with the wild-type plant enzyme acetohydroxyacid synthase. This line of rice plants was developed by exposing rice seeds to the mutagen methanesulfonic acid ethyl ester (EMS), and screening millions of progeny for herbicide resistance. See also the present inventor's U.S. Pat. Nos. 5,736, 629, 5,773,704, 5,952,553, and 6,274,796.

U.S. Pat. No. 4,443,971 discloses a method for preparing herbicide tolerant plants by tissue culture in the presence of herbicide. U.S. Pat. No. 4,774,381 discloses sulfonylurea (sulfonamide) herbicide-resistant tobacco plants prepared in such a manner.

U.S. Pat. No. 5,773,702 discloses sugar beets with a resistant mutant AHAS enzyme, derived from cell cultures grown in the presence of herbicide.

U.S. Pat. No. 5,633,437 discloses a herbicide resistant AHAS enzyme and gene isolated from cockleburs.

U.S. Pat. No. 5,767,361 discloses a mutant, resistant AHAS enzyme from maize. The definitions of the U.S. Pat. No. 5,767,361 patent are incorporated into the present disclosure by reference, to the extent that those definitions are not inconsistent with the present disclosure. See also U.S. Pat. No. 5,731,180 and European Patent Application 0 525 384 A2.

U.S. Pat. No. 5,605,011; European Patent Application 0 257 993 A2; and European Patent Application 0 730 030 A1 disclose resistant acetolactate synthase (ALS, another name for AHAS) enzymes based on enzymes derived from callus culture of tobacco cells in the presence of herbicide, from spontaneous mutations of the ALS gene in yeast; EMS-induced mutations in *Arabidopsis* seeds; certain modifications of those enzymes; and the transformation of various plants with genes encoding the resistant enzymes. These patents disclose several techniques for modifying AHAS genes to produce herbicide-resistant AHAS enzymes, and for transforming plants with those genes.

U.S. Pat. Re 35,661 (a reissue of U.S. Pat. No. 5,198,599) discloses lettuce plants with enhanced resistance to herbicides that target the enzyme acetolactate synthase. The initial source of herbicide resistance was a prickly lettuce weed infestation in a grower's field, an infestation that was not controlled with commercial sulfonylurea herbicides.

DISCLOSURE OF INVENTION

I have discovered multiple lines of novel herbicide resistance in rice plants, and improved methods for generating herbicide resistance in rice plants generally. The novel resistant rice has pre-emergence resistance, post-emergence resistance, or both pre-emergence resistance and post-emergence resistance to herbicides that are effective against red rice. The isolated novel rice lines have to date demonstrated resistance to the following herbicides: imazethapyr, imazapic, imazapyr, imazamox, sulfometuron methyl, imazaquin, chlorimuron ethyl, metsulfuron methyl, rimsulfuron, thifensulfuron methyl, pyrithiobac sodium, tribenuron methyl, and nicosulfuron. The novel rice is also expected to be resistant to derivatives of these herbicides, and to at least some of the other herbicides that normally inhibit acetohydroxyacid synthase (AHAS), particularly imidazolinone and sulfonylurea herbicides. The herbicidal activity of each of the above herbicides is known to be due to its effect on the acetohydroxyacid synthase (AHAS) enzyme. This enzyme catalyzes the first step in the synthesis of the amino acids leucine, valine, and isoleucine. Inhibition of the AHAS enzyme is normally fatal to plants.

Besides controlling red rice, many AHAS-inhibiting herbicides also effectively control other weeds commonly found in rice fields. Several of these herbicides have residual activity, so that one treatment controls both existing weeds and weeds that sprout later—a significant advantage in rice production. No herbicide currently labelled for use on rice has residual activity against a broad spectrum of weeds including red rice. With effective residual activity against red rice and other weeds, rice producers now have a weed control system far superior to those currently used.

One role of water in rice production is in weed control—a layer of standing water in the rice field inhibits the growth of weeds. With a herbicide having residual weed control properties, producers will have much greater flexibility in water management. Flooding of fields may now be delayed, which in turn will help control the rice water weevil, a primary insect pest of rice. Alternatively, or perhaps in conjunction, pumping costs could be reduced by delaying flooding until sufficient rain falls to flood a field at no cost to the producer.

Although the resistance mechanisms of the new rice lines have not yet been fully characterized, it is believed that the herbicide resistance of the novel rice lines is most likely attributable to different mutations of the AHAS enzyme, mutations resulting in enzymes expressing direct resistance to levels of herbicide that normally inhibit the wild-type AHAS enzyme. That the resistance is due to mutant AHAS enzymes (rather than another route such as gene copy number, enhanced promoter activity, metabolic degradation, etc.) will be confirmed using in vitro assays. The procedures used to assay the activity of the acetohydroxyacid synthases will be substantially as described in B. K. Singh et al., "Assay of Acetohydroxyacid Synthase," *Analytical Biochemistry*, vol. 171, pp. 173-179 (1988), except as noted. In the first paragraph of Singh's "Materials and Methods," instead of corn suspension culture cells, stem tissues from greenhouse-grown rice seedlings at the four-leaf stage of development will be used. Leaf blades will be removed, and 40.0 grams (fresh weight) of tissue will be extracted in the same manner for each of the breeding lines. At the suggestion of the first author, B. K. Singh (personal communication), the desalting step mentioned at the bottom of Singh's first column under "Materials and Methods" will be eliminated. Pursuit™ herbicide (imazethapyr) will be included in the "standard reaction mixture" for the AHAS assay in various concentrations. Colorimetric absorbance will be measured at 520 nm. Checks will be made of direct acetoin formation during the enzyme assay. Each treatment will be conducted in two replicates.

An alternative AHAS assay is that disclosed in U.S. Pat. No. 5,605,011, at col. 53, line 61 through col. 54, line 37.

MODES FOR CARRYING OUT THE INVENTION

A total of 27 new rice lines expressing resistance to AHAS-inhibiting herbicides were identified, following exposure of rice seeds to the mutagen methanesulfonic acid ethyl ester (EMS). Additional resistant rice lines will be developed and identified using similar mutation and screening techniques. Other strong mutagens known in the art may be substituted for EMS in generating such mutations, for example, nitrosoquanidine, ethylnitrosourea, ionizing radiation (such as X-rays, gamma rays, or UV), or radiomimetic compounds such as bleomycins, etoposide, and teniposide. (Bleomycins, for example, are glycopeptide antibiotics isolated from strains of *Streptomyces verticillus*. One bleomycin is sold under the trademark Blenoxane® by Bristol Laboratories, Syracuse, N.Y.)

EXAMPLES 1-15

Approximately 52 million mutated ($M_2$) rice seed were screened. The mutated seed were developed by soaking a total of 340 pounds of seed ($M_1$), of the rice cultivars "Cypress" or "Bengal," in a 0.175% (by weight) aqueous solution of EMS. Approximately 170 lbs. of rice were exposed to EMS for 16 hours; approximately 85 lbs. were exposed for 24 hours; and approximately 85 lbs were exposed for 35 hours. Seed from the three exposure regimens were pooled for the screening experiments described below.

Following EMS treatment, the $M_1$ seed were thoroughly rinsed with water and drained before being planted by broadcast-seeding into shallow water, water that was drained 24 hours later. The field was re-flooded three days later, and the field was maintained in a flooded condition until it was drained for harvesting. The harvested $M_2$ seed were stored over the winter, and were screened for herbicide resistance the following spring. Following drill-seeding of the approximately 52 million $M_2$ seed, a pre-emergence application of imazethapyr at a rate of 0.125 lb ai/A (pounds of active ingredient per acre) was applied prior to the first flush. A post-emergence treatment of imazethapyr at 0.063 lb ai/A was applied when the rice reached the 3-leaf stage. The fifteen $M_2$ plants that survived the herbicide application were collected and transferred to the greenhouse.

The herbicide resistance of the progeny of these plants ($M_3$) was confirmed through a post-emergence application of 0.125 lb ai/A imazethapyr at the 3-leaf stage in the greenhouse. The 15 resistant plants of 52 million total $M_2$ plants represent a success rate of approximately 1 imidazolinone-resistant mutant identified per 3.5 million mutated seeds screened.

$M_4$ progeny seed were collected from the resistant $M_3$ plants, and were used in a field test. The field test comprised 8 replicate sets. Each of the sets contained 100 rows four feet in length. Each of the sets had 74 rows of the $M_4$ resistant lines. Each set had multiple rows of each of the 15 resistant lines, with the number of rows of each of the lines varying due to the different numbers of seeds that were available for each at the time. Each of the replicate sets also contained 16 rows of the non-resistant cultivar "Cypress" as a negative control, and 10 rows of earlier-developed herbicide-resistant rice lines as positive controls. (The positive controls were either ATCC 97523 or a hybrid of ATCC 97523 and ATCC 75295.)

A different herbicide treatment was applied post-emergence to each of these eight replicate sets when the rice reached the 3 leaf stage. The control set was treated with 4 quarts/acre of Arrosolo™. Arrosolo™ is a herbicide that is currently used commercially with conventional rice varieties. The remaining 7 sets were treated with imidazolinone herbicides as follows: (1) imazethapyr (trade name Pursuit™) at 0.125 lb ai/A; (2) imazethapyr at 0.188 lb ai/A; (3) imazapic (trade name Cadre™) at 0.063 lb ai/A; (4) imazapic at 0.125 lb ai/A; (5) imazapyr (trade name Arsenal™) at 0.05 lb ai/A; (6) imazapyr at 0.09 lb ai/A; and (7) a mixture of 75% imazethapyr and 25% imazapyr (trade name Lightning™) at 0.052 lb ai/A.

Note that all herbicide application rates tested were equal to or greater than the recommended application rates for the use of the same herbicides on other crops.

Levels of resistance to herbicide were determined both at three weeks after spraying, and at maturity. No row was significantly injured by the control treatment with the conventional rice herbicide Arrosolo™. By contrast, each of the seven imidazolinone treatments resulted in 100% control of the rows of non-resistant Cypress rice, without a single surviving plant among any of the 112 treated rows. Each of the herbicide-resistant $M_4$ progeny rows in each of the sets, and each of the herbicide-resistant positive controls in each of the sets, displayed insignificant injury or no injury from the various imidazolinone treatments. The rows of resistant $M_4$ progeny treated with the imidazolinones, and the rows of herbicide-resistant positive controls treated with the imidazolinones, were visually indistinguishable from the Arrosolo™-treated rows with respect to height, vigor, days to maturity, and lack of visible herbicide injury.

Samples of the seed harvested from each of the fifteen lines of the $M_4$ progeny, i.e., samples of $M_5$ seed from each of the fifteen separate lines; lines designated by the inventor as SSC01, SSC02, SSC03, SSC04, SSC05, SSC06, SSC07, SSC08, SSC09, SSC10, SSC11, SSC12, SSC13, SSC14, and SSC15; were separately deposited with the American Type Culture Collection (ATCC), 10801 University Boulevard, Manassas, Va. 20110-2209 on Nov. 5, 1998; and were assigned ATCC Accession Nos. 203419, 203420, 203421, 203422, 203423, 203424, 203425, 203426, 203427, 203428, 203429, 203430, 203431, 203432, and 203433, respectively. Each of these deposits was made pursuant to a contract between ATCC and the assignee of this patent application, Board of Supervisors of Louisiana State University and Agricultural and Mechanical College. Each of the contracts with ATCC provides for permanent and unrestricted availability of these seeds or the progeny of these seeds to the public on the issuance of the U.S. patent describing and identifying the deposit or the publication or the laying open to the public of any U.S. or foreign patent application, whichever comes first, and for the availability of these seeds to one determined by the U.S. Commissioner of Patents and Trademarks (or by any counterpart to the Commissioner in any patent office in any other country) to be entitled thereto under pertinent statutes and regulations. The assignee of the present application has agreed that if any of the seeds on deposit should become nonviable or be lost or destroyed when cultivated under suitable conditions, they will be promptly replaced on notification with a viable sample of the same seeds.

EXAMPLES 16-27

Approximately 60 million additional mutated ($M_2$) rice seed were screened. The mutated seed were developed by soaking a total of 300 pounds of seed ($M_1$) of the rice cultivar "Cypress" in a 0.175% (by weight) aqueous solution of the mutagen EMS for 23 hours.

Following EMS treatment the $M_1$ seed were thoroughly rinsed with water and drained before being planted by broadcast-seeding into shallow water, water that was drained 24 hours later. The field was re-flooded three days later, and the field was maintained in a flooded condition until it was drained for harvesting. The harvested $M_2$ seed were stored over the winter, and were screened for herbicide resistance the following spring. Following broadcast-seeding and shallow soil incorporation of approximately 60 million $M_2$ seed, a post-emergence application of imazapic (trade name Cadre™) at 0.125 lb ai/A was sprayed on half the field, and a post-emergence application of imazapyr (trade name Arsenal™) at 0.10 lb ai/A was applied to the remaining half of the field at the three-leaf stage. The twenty-three $M_2$ plants that survived the herbicide application were collected and transferred to the greenhouse. Later testing (described below) showed that twelve of these plants represented new herbicide resistant lines; the other plants were either "escapes" (plants receiving no herbicide spray), or "volunteer" seed of the ATCC 97523 line that had remained in the soil from a prior season.

The 12 resistant plants of 60 million total $M_2$ plants represent a success rate of approximately 1 imidazolinone-resistant mutant identified per 5 million mutated seeds screened.

The herbicide resistance of the progeny of these plants ($M_3$) was confirmed with the following herbicide applications in the greenhouse: 0.125 lb ai/A imazethapyr (trade name Pursuit™) as a pre-emergence application; 0.063 lb ai/A imazethapyr as a post-emergence application; 0.10 lb ai/A sulfometuron methyl (trade name Oust™) as a pre-emergence application; 0.05 lb ai/A sulfometuron methyl as a post-emergence application; 0.10 lb ai/A nicosulfuron (trade name Accent™) applied pre-emergence; and 0.05 lb ai/A nicosulfuron applied post-emergence. Two $M_3$ seed from each of the twenty-three herbicide-resistant lines were planted in each of four replicate pots for each treatment. Equivalent plantings of control lines were made with (non-resistant) Cypress and Bengal rice seeds.

Samples of the seed harvested from several of these lines of the $M_4$ progeny; namely, samples of $M_5$ seed from each of the seven separate lines designated by the inventor as PWC16, PWC23, CMC29, CMC31, WDC33, WDC37, and WDC38; were separately deposited with the American Type Culture Collection (ATCC), 10801 University Boulevard, Manassas, Va. 20110-2209 on Nov. 2, 1999; and were assigned ATCC Accession Nos. PTA-904, PTA-905, PTA-902, PTA-903, PTA-906, PTA-907, and PTA-908, respectively. Each of these deposits was made pursuant to a contract between ATCC and the assignee of this patent application, Board of Supervisors of Louisiana State University and Agricultural and Mechanical College. Each of the contracts with ATCC provides for permanent and unrestricted availability of these seeds or the progeny of these seeds to the public on the issuance of the U.S. patent describing and identifying the deposit or the publication or the laying open to the public of any U.S. or foreign patent application, whichever comes first, and for the availability of these seeds to one determined by the U.S. Commissioner of Patents and Trademarks (or by any counterpart to the Commissioner in any patent office in any other country) to be entitled thereto under pertinent statutes and regulations. The assignee of the present application has agreed that if any of the seeds on deposit should become nonviable or be lost or destroyed when cultivated under suitable conditions, they will be promptly replaced on notification with a viable sample of the same seeds.

Five other lines, designated by the inventor as PWC17, PWC19, PWC21, PWC22, and CMC27, exhibited lower levels of herbicide resistance. These lines appear to differ both from the lines that have now been deposited with ATCC, and from prior line ATCC 97523. Due to their lower levels of resistance, these lines had not been deposited with ATCC as of the international filing date of the present application. However, these lines may have potential value as breeding material to cross with other sources of herbicide resistance, or with each other, in order to enhance total levels of resistance. If these five lines involve different resistance mechanisms, or different AHAS isozymes as compared to the ATCC-deposited lines, then crossing one of these lines with one of the ATCC-deposited lines could result in a hybrid with an enhanced total level of resistance. Their herbicide resistance levels would not, however, appear to make any of these five lines, standing alone, suitable candidates for breeding new herbicide resistant rice lines.

Further Field Tests and Greenhouse Tests

Further field tests and greenhouse tests were conducted to evaluate the tolerance of the resistant lines. The field tests included both pre-emergence and post-emergence herbicide application studies. The same lines were included in both studies, except that line WDC37 was included in the pre-emergence study only, due to the lack of sufficient quantity of seed at the time.

The herbicides applied as pre-emergence applications were imazaquin, imazethapyr, and imazapic. Each treatment was applied to each of two replicate plots. Each replicate plot contained three-foot long rows of each herbicide resistant line, along with a check row of non-resistant rice. Two plots were left unsprayed to serve as untreated controls. All herbicide-resistant lines exhibited little or no injury from the herbicide applications. All check rows of the non-resistant rice variety Cypress, by contrast, were either killed or severely injured in all plots given herbicide treatments.

Post-emergence application was studied in fifty replicate plots of the same herbicide-resistant lines, except that line WDC37 was not included in the post-emergence field study. For the post-emergence field study, each herbicide treatment was applied to each of two replicate plots. Four plots were left unsprayed to serve as untreated controls. Herbicide treatments studied post-emergence were imazethapyr (Pursuit™), imazapic (Cadre™), imazamox (Raptor™), a 1:1 (by weight) mixture of imazapic and imazapyr, a 3:1 (by weight) mixture of imazapic (Cadre™) and imazapyr (Arsenal™), imazapyr (Arsenal™), chlorimuron ethyl (Classic™), metsulfuron methyl (Ally™), nicosulfuron (Accent™), rimsulfuron (Matrix™), a 2:1 mixture (by weight) (Harmony Extra™) of thifensulfuron methyl and tribenuron methyl, and pyrithiobac sodium (Staple™).

The greenhouse tests comprised two replicate studies using the same herbicides and rates as were used in the post-emergence field test. The greenhouse studies evaluated the post-emergence herbicide resistance of a few lines for which the quantity of seed then available was inadequate to include in the field tests. Seeds of the resistant lines were planted in 2 inch×2 inch peat pots, and the seedlings were then sprayed at the 3-4 leaf stage. Non-resistant check lines were included for comparison. As in the field tests, the non-resistant checks were either killed or severely injured by the herbicide treatments.

The results of these field and greenhouse studies are summarized in Tables 3 and 4.

RESULTS AND DISCUSSION

Previous selections for imidazolinone-resistant rice by screening following seed exposure to EMS had resulted in fewer resistant rice lines. For example, screening approximately 35 million $M_2$ seed following exposure of the $M_1$ seed to 0.5% EMS for 16 hours resulted in a single herbicide-resistant mutant plant, for a success ratio of 1 resistant mutant per 35 million mutated seed. By contrast, each of the two series of screenings reported here had a significantly higher rate of successfully producing herbicide-resistant mutants. It is believed, without wishing to be bound by this theory, that the improved efficiency was due to the difference in mutagen concentrations and exposure times used.

The more efficient mutation protocols described here used a relatively longer exposure to a relatively lower concentration of mutagen than had previously been used. In Examples 1-15 the average mutagen exposure time was 22.75 hours, and the EMS concentration was 0.175%. This represents a 42% longer average exposure time, and a 65% reduction in the mutagen concentration, as compared to the only successful event from the earlier screening of 35 million seeds. The result was a ten-fold increase in the rate of resistant mutant recovery (one per 3.5 million seed versus one per 35 million seed).

Examples 16-27 used conditions similar to those for Examples 1-15, and were also more efficient in producing resistant mutants. The same EMS mutagen concentration (0.175%) was used, and only a slightly different exposure time (23 hours versus an average of 22.75 hours). The herbicide-resistant mutant production rate in this trial was 1 plant per 5 million seed. These results indicate that longer exposures to lower mutagen concentrations appear generally to produce higher rates of successful herbicide resistant mutants.

Each of the resistant mutants from these two screenings exhibits resistance to one or more imidazolinone and sulfonylurea herbicides. A summary of the herbicide application used in the initial screening for resistance is given in Table 1. The results of the field tests for Examples 1-15 (SSC01 through SSC15) are given in Table 2. The results of the field tests for Examples 16-27 (those resistant lines having PWC, CMC, or WDC designations) are given in Tables 3 and 4. Note that the application rates in Tables 1, 2, and 3 are given in pounds of active ingredient per acre, while the rates in Table 4 are given in ounces of active ingredient per acre.

TABLE 1

Screening Herbicide Application

| Line | Imazethapyr 0.125 pre-emerge + 0.063 post-emerge (lb ai/A) | Imazapyr 0.10 post-emerge (lb ai/A) | Imazameth 0.125 post-emerge (lb ai/A) |
|---|---|---|---|
| SSC01 | X | | |
| SSC02 | X | | |
| SSC03 | X | | |
| SSC04 | X | | |
| SSC05 | X | | |
| SSC06 | X | | |
| SSC07 | X | | |
| SSC08 | X | | |
| SSC09 | X | | |
| SSC10 | X | | |
| SSC11 | X | | |
| SSC12 | X | | |
| SSC13 | X | | |
| SSC14 | X | | |
| SSC15 | X | | |
| PWC16 | | X | |
| PWC17 | | X | |
| PWC18 | | X | |
| PWC19 | | X | |
| PWC20 | | X | |
| PWC21 | | X | |
| PWC22 | | X | |
| PWC23 | | X | |
| PWC24 | | X | |
| CMC25 | | | X |
| CMC26 | | | X |
| CMC27 | | | X |
| CMC28 | | | X |
| CMC29 | | | X |
| CMC30 | | | X |
| CMC31 | | | X |
| WDC32 | | | X |
| WDC33 | | | X |
| WDC34 | | | X |
| WDC35 | | | X |
| WDC36 | | | X |
| WDC37 | | | X |
| WDC38 | | | X |

TABLE 2

Post-Screening Herbicide Testing

Herbicide Application Rate (lb ai/A); & whether applied pre-emergence or post-emergence

| Line | Imazethapyr | | | | Imazapyr | | Imazameth | | Imazethapyr (75%) + Imazapyr (25%) | Sulfometuron Methyl | | Nicosulfuron | |
|---|---|---|---|---|---|---|---|---|---|---|---|---|---|
| | 0.125 pre | 0.063 post | 0.125 post | 0.188 post | 0.05 post | 0.09 post | 0.063 post | 0.125 post | 0.052 post | 0.10 pre | 0.05 post | 0.10 pre | 0.05 post |
| SSC01 ATCC 203419 | X | X | X | X | X | X | X | X | X | 0 | 0 | X | X |
| SSC02 ATCC 203420 | X | X | X | X | X | X | X | X | X | 0 | 0 | X | X |
| SSC03 ATCC 203421 | X | X | X | X | X | X | X | X | X | 0 | 0 | X | X |
| SSC04 ATCC 203422 | X | X | X | X | X | X | X | X | X | X | 0 | X | X |
| SSC05 ATCC 203423 | X | X | X | X | X | X | X | X | X | 0 | 0 | X | X |
| SSC06 ATCC 203424 | X | X | X | X | X | X | X | X | X | X | 0 | X | X |
| SSC07 ATCC 203425 | X | X | X | X | X | X | X | X | X | 0 | 0 | X | X |
| SSC08 ATCC 203426 | X | X | X | X | X | X | X | X | X | X | 0 | X | X |
| SSC09 ATCC 203427 | X | X | X | X | X | X | X | X | X | 0 | 0 | X | X |
| SSC10 ATCC 203428 | X | X | X | X | X | X | X | X | X | X | 0 | X | X |
| SSC11 ATCC 203429 | X | X | X | X | X | X | X | X | X | 0 | 0 | X | X |

TABLE 2-continued

Post-Screening Herbicide Testing

Herbicide Application Rate (lb ai/A); & whether applied pre-emergence or post-emergence

| Line | Imazethapyr | | | | Imazapyr | | Imazameth | | Imazethapyr (75%) + Imazapyr (25%) | Sulfometuron Methyl | | Nicosulfuron | |
|---|---|---|---|---|---|---|---|---|---|---|---|---|---|
| | 0.125 pre | 0.063 post | 0.125 post | 0.188 post | 0.05 post | 0.09 post | 0.063 post | 0.125 post | 0.052 post | 0.10 pre | 0.05 post | 0.10 pre | 0.05 post |
| SSC12 ATCC 203430 | X | X | X | X | X | X | X | X | X | 0 | 0 | X | X |
| SSC13 ATCC 203431 | X | X | X | X | X | X | X | X | X | 0 | 0 | X | X |
| SSC14 ATCC 203432 | X | X | X | X | X | X | X | X | X | 0 | 0 | X | X |
| SSC15 ATCC 203433 | X | X | X | X | X | X | X | X | X | 0 | 0 | X | X |
| PWC16 ATCC PTA-904 | X | X | | | | | | | | 0 | 0 | X | X |
| PWC17 | X | X | | | | | | | | X | 0 | X | X |
| PWC18 | X | X | | | | | | | | 0 | 0 | X | X |
| PWC19 | X | X | | | | | | | | 0 | 0 | X | X |
| PWC20 | X | X | | | | | | | | 0 | 0 | X | X |
| PWC21 | X | X | | | | | | | | 0 | 0 | X | X |
| PWC22 | | X | | | | | | | | | | | |
| PWC23 ATCC PTA-905 | X | X | | | | | | | | X | X | X | X |
| PWC24 | X | X | | | | | | | | X | 0 | X | X |
| CMC25 | X | X | | | | | | | | X | 0 | X | X |
| CMC26 | X | X | | | | | | | | 0 | 0 | X | X |
| CMC27 | | | | | | | | | | | | | |
| CMC28 | X | X | | | | | | | | 0 | 0 | X | X |
| CMC29 ATCC PTA-902 | X | X | | | | | | | | 0 | 0 | X | X |
| CMC30 | X | X | | | | | | | | 0 | 0 | X | X |
| CMC31 ATCC PTA-903 | X | X | | | | | | | | 0 | 0 | X | X |
| WDC32 | X | X | | | | | | | | X | X | X | X |
| WDC33 ATCC PTA-906 | X | X | | | | | | | | 0 | 0 | X | X |
| WDC34 | X | X | | | | | | | | X | 0 | X | X |
| WDC35 | X | X | | | | | | | | 0 | 0 | X | X |
| WDC36 | X | X | | | | | | | | 0 | 0 | X | X |
| WDC37 ATCC PTA-907 | X | X | | | | | | | | 0 | 0 | X | X |
| WDC38 ATCC PTA-908 | X | X | | | | | | | | 0 | 0 | X | X |

Notes to Table 2:
X = resistant;
0 = sensitive (exhibited wild-type reaction to herbicide);
blank = not yet tested.

TABLE 3

Post-Screening Herbicide Testing

Herbicide Application Rate (lb ai/A); & whether applied pre-emergence or post-emergence

| Line | Imazethapyr | | | | | Imazapic | | | | | Imazaquin | | | Imazamox | | Imazapic 0.05 + Imazapyr |
|---|---|---|---|---|---|---|---|---|---|---|---|---|---|---|---|---|
| | 0.063 pre | 0.125 pre | 0.188 pre | 0.063 post | 0.125 post | 0.037 pre | 0.075 pre | 0.15 pre | 0.075 post | 0.15 post | 0.125 pre | 0.25 pre | 0.375 pre | 0.05 post | 0.10 post | 0.05 post |
| SSC01 ATCC 203419 | X | X | X | X | X | X | X | X | X | X | X | X | X | X | X | X |
| SSC02 ATCC 203420 | X | X | X | X | X | X | X | X | X | X | X | X | X | X | X | X |
| SSC03 ATCC 203421 | X | X | X | X | X | X | X | X | X | X | X | X | X | X | X | X |
| SSC04 ATCC 203422 | X | X | X | X | X | X | X | X | X | X | X | X | X | X | X | X |
| SSC05 ATCC 203423 | X | X | X | X | X | X | X | X | X | X | X | X | X | X | X | X |
| SSC06 ATCC 203424 | X | X | X | X | X | X | X | X | X | X | X | X | X | X | X | X |
| SSC07 ATCC 203425 | X | X | X | X | X | X | X | X | X | X | X | X | X | X | 0 | X |
| SSC08 ATCC 203426 | X | X | X | X | X | X | X | X | X | X | X | X | X | X | X | X |
| SSC09 ATCC 203427 | X | X | X | X | X | X | X | X | X | X | X | X | X | X | X | X |
| SSC10 ATCC 203428 | X | X | X | X | X | X | X | X | X | X | X | X | X | X | X | X |
| SSC11 ATCC 203429 | X | X | X | X | X | X | X | X | X | X | X | X | X | X | X | X |
| SSC12 ATCC 203430 | X | X | X | X | X | X | X | X | X | X | X | X | X | X | X | X |
| SSC13 ATCC 203431 | X | X | X | X | X | X | X | X | X | X | X | X | X | X | 0 | X |
| SSC14 ATCC 203432 | X | X | X | X | X | X | X | X | X | X | X | X | X | X | 0 | X |
| SSC15 ATCC 203433 | X | X | X | X | X | X | X | X | X | X | X | X | X | X | 0 | X |
| PWC16 ATCC PTA-904 | X | X | X | X | X | X | X | X | X | X | X | X | X | X | X | X |
| PWC23 ATCC PTA-905 | X | X | X | X | X | X | X | X | X | X | X | X | X | X | X | X |
| CMC29 ATCC PTA-902 | X | X | X | X | X | X | X | X | X | X | X | X | X | X | X | X |
| CMC31 ATCC PTA-903 | X | X | X | X | X | X | X | X | X | X | X | X | X | X | X | X |
| WDC33 ATCC PTA-906 | | | | X | X | | | | X | X | | | | X | X | X |
| WDC37 ATCC PTA-907 | X | X | X | | | X | X | X | | | X | X | X | | | |

TABLE 3-continued

Post-Screening Herbicide Testing

| | | | | | | | | | | | | | | | | | |
|---|---|---|---|---|---|---|---|---|---|---|---|---|---|---|---|---|---|
| WDC38 ATCC PTA-908 | X | X | X | X | X | X | X | X | X | X | X | X | X | X | X | | X |

| | Herbicide Application Rate (lb ai/A); & whether applied pre-emergence or post-emergence | | | |
|---|---|---|---|---|
| | Imazapic 0.075 + Imazapyr 0.025 | Imazapic 0.15 + Imazapyr 0.05 | Imazapyr | |
| Line | post | post | 0.05 post | 0.10 post |
| SSC01 ATCC 203419 | X | X | X | X |
| SSC02 ATCC 203420 | X | X | X | X |
| SSC03 ATCC 203421 | X | X | X | X |
| SSC04 ATCC 203422 | X | X | X | X |
| SSC05 ATCC 203423 | X | X | X | X |
| SSC06 ATCC 203424 | X | X | X | X |
| SSC07 ATCC 203425 | X | X | X | X |
| SSC08 ATCC 203426 | X | X | X | X |
| SSC09 ATCC 203427 | X | X | X | X |
| SSC10 ATCC 203428 | X | X | X | X |
| SSC11 ATCC 203429 | X | X | X | X |
| SSC12 ATCC 203430 | X | X | X | X |
| SSC13 ATCC 203431 | X | X | X | X |
| SSC14 ATCC 203432 | X | X | X | X |
| SSC15 ATCC 203433 | X | X | X | X |
| PWC16 ATCC PTA-904 | X | X | X | X |
| PWC23 ATCC PTA-905 | X | X | X | X |
| CMC29 ATCC PTA-902 | X | X | X | X |
| CMC31 ATCC PTA-903 | X | X | X | X |
| WDC33 ATCC PTA-906 | X | X | X | X |
| WDC37 ATCC PTA-907 | | | | |

TABLE 3-continued

Post-Screening Herbicide Testing

| | | | | |
|---|---|---|---|---|
| WDC38 ATCC PTA-908 | X | X | X | X |

Notes to Table 3:
X = resistant;
0 = sensitive (exhibited wild-type reaction to herbicide);
blank = not yet tested.

TABLE 4

Post-Screening Herbicide Testing

Herbicide Application Rate (ounces ai/A); & whether applied pre-emergence or post-emergence

| Line | Chlorimuron Ethyl | | Metsulfuron Methyl | | Nicosulfuron | | Rimsulfuron | | Thifensulfuron methyl (66.7%) + tribenuron methyl (33.3%) | | Pyrithiobac sodium | |
|---|---|---|---|---|---|---|---|---|---|---|---|---|
| | 0.125 post | 0.250 post | 0.06 post | 0.12 post | 0.5 post | 1.0 post | 0.20 post | 0.40 post | 0.45 post | 0.90 post | 1.0 post | 2.0 post |
| SSC01 ATCC 203419 | X | X | X | X | X | X | X | X | X | X | X | X |
| SSC02 ATCC 203420 | X | X | X | X | X | X | X | X | X | X | X | X |
| SSC03 ATCC 203421 | X | X | X | X | X | X | X | X | X | X | X | X |
| SSC04 ATCC 203422 | X | X | X | X | X | X | X | X | X | X | X | X |
| SSC05 ATCC 203423 | X | X | X | X | X | X | X | X | X | X | X | X |
| SSC06 ATCC 203424 | X | X | X | X | X | X | X | X | X | X | X | X |
| SSC07 ATCC 203425 | X | X | X | X | X | X | X | X | X | X | X | X |
| SSC08 ATCC 203426 | X | X | X | X | X | X | X | X | X | X | X | X |
| SSC09 ATCC 203427 | X | X | X | X | X | X | X | X | X | X | X | X |
| SSC10 ATCC 203428 | X | X | X | X | X | X | X | X | X | X | X | X |
| SSC11 ATCC 203429 | X | X | X | X | X | X | X | X | X | X | X | X |
| SSC12 ATCC 203430 | X | X | X | X | X | X | X | X | X | X | X | X |
| SSC13 ATCC 203431 | X | X | X | X | X | X | X | X | X | X | X | X |
| SSC14 ATCC 203432 | X | X | X | X | X | X | X | X | X | X | X | X |
| SSC15 ATCC 203433 | X | X | X | X | X | X | X | X | X | X | X | X |
| PWC16 ATCC PTA-904 | 0 | 0 | X | X | X | 0 | 0 | 0 | X | X | X | X |
| PWC23 ATCC PTA-905 | 0 | 0 | X | X | X | 0 | 0 | 0 | X | X | X | X |
| CMC29 ATCC PTA-902 | 0 | 0 | 0 | X | X | 0 | 0 | 0 | X | X | X | X |

TABLE 4-continued

Post-Screening Herbicide Testing

Herbicide Application Rate (ounces ai/A); & whether applied pre-emergence or post-emergence

| Line | Chlorimuron Ethyl | | Metsulfuron Methyl | | Nicosulfuron | | Rimsulfuron | | Thifensulfuron methyl (66.7%) + tribenuron methyl (33.3%) | | Pyrithiobac sodium | |
|---|---|---|---|---|---|---|---|---|---|---|---|---|
| | 0.125 post | 0.250 post | 0.06 post | 0.12 post | 0.5 post | 1.0 post | 0.20 post | 0.40 post | 0.45 post | 0.90 post | 1.0 post | 2.0 post |
| CMC31 ATCC PTA-903 | 0 | 0 | 0 | X | X | X | 0 | 0 | X | X | X | X |
| WDC33 ATCC PTA-906 | X | X | X | X | 0 | 0 | 0 | 0 | X | X | X | X |
| WDC37 ATCC PTA-907 | | | | | | | | | | | | |
| WDC38 ATCC PTA-908 | 0 | 0 | 0 | X | X | X | 0 | 0 | 0 | X | X | X |

Notes to Table 4:
X = resistant;
0 = sensitive (exhibited wild-type reaction to herbicide);
blank = not yet tested.
In the entries for CMC29, CMC31, and WDC38 for metsulfuron methyl, and also for WDC38 (only) for the thifensulfuron methyl - tribenuron methyl mixture, at the lower rate of application, the response was identical to that of the wild-type, with all surviving the lower rate of application; while at the higher rate of application, the wild-type plants were seriously injured, and the CMC29, CMC31, and WDC38 lines exhibited substantially less injury.

Further examination of these plants led to the conclusion that the following herbicide resistant lines appeared to be identical to prior herbicide resistant line ATCC 97523, presumably because a few seeds of ATCC 97523 from prior trials had remained dormant in the soil between growing seasons: PWC18, PWC20, PWC24, CMC25, CMC26, CMC28, CMC30, WDC32, WDC34, WDC35, and WDC36.

Enhanced resistance will result from crossing the novel rice lines with one another. Enhanced resistance will also result from the synergy of crossing one or more of the novel rice lines, with their resistant AHAS enzymes, with the metabolic-based resistant rice lines disclosed in U.S. Pat. No. 5,545,822, as typified by the rice having ATCC accession number 75295. As disclosed in the present inventor's published international application WO 97/41218, such synergy has been seen in hybrids of the rice having ATCC accession number 75295 with the rice having ATCC accession number 97523, the latter having a mutant, resistant AHAS enzyme in rice.

Notes on Mutation Selection Procedures in the Field

The following procedures were used for screening large quantities of mutated rice seed for herbicide resistance in the field.

Exposure to mutagen or to conditions conducive to the induction of mutations may be performed at different stages of growth and different culture conditions, e.g., exposing dry seed, seed sprouted in water for 24 hours, or seed sprouted in water for 48 hours, etc. to mutagen; or growing cells in tissue culture, such as another culture, with or without the application of mutagen; etc.

Rice to be planted for seed is ordinarily cleaned after harvest. Once cleaning is completed, any standard planting equipment can be satisfactorily used. However, this laborious and time-consuming cleaning step can be bypassed if the planting equipment will tolerate the pieces of straw and other extraneous material that typically accompany combine-harvested rice. Eliminating the cleaning step allows generations of seed to be grown, screened, and increased more rapidly. For example, using a spinner/spreader attachment on a tractor allows broadcast planting of rice that is accompanied by a moderate amount of extraneous material. Broadcast planting is also more rapid than drill-seeding, saving further time and labor. Seed planted with a spinner/spreader can either be lightly incorporated into the soil following broadcast-spreading, or allowed to remain on the soil surface, in which case it must be kept sufficiently moist by irrigation if rainfall is inadequate.

Freshly-harvested rice seed may have a degree of dormancy, which prevents some of the otherwise viable seed from sprouting immediately. This dormancy normally disappears during storage. However, if the harvested seed is to be planted for selection purposes shortly after harvest to accelerate generation time, then treatment to reduce or eliminate dormancy is beneficial. One method to eliminate dormancy is to expose the seed to a temperature of about 50° C. for about five days. Moisture should be allowed to escape from the seed during this treatment, so relatively small containers of moisture-permeable material should be used, such as cloth bags. Alternatively, stems with panicles still attached may be positioned to allow air to circulate over the panicles, for example, by standing them upright in a paper bag. As a further alternative, forced-air drying may be used, with or without storage in bags, provided that the seed is situated so that moisture is not entrapped around sections of the grain.

When spraying mutated rice seed or plants to identify resistant individuals, it is important to achieve as uniform and precise a treatment as possible. Since the number of true resistant individuals will be a very small fraction of the total number of seeds, even a small fraction of "escapes" (i.e., false positives, plants fortuitously not receiving any herbicide) can complicate and retard the screening process. Therefore the herbicide-spraying equipment should be in good condition, and should be calibrated as accurately as possible. Each spray nozzle along the spraying boom should deliver spray at the same volumetric rate. Nozzles should be accurately aligned to avoid insufficient spray overlap between nozzles. Relatively short tractor spray booms (for example, approximately 12 feet) are helpful in minimizing undesirable boom movements while spraying.

Appropriate nozzles include the following, each of which has a flat spray tip, and sprays approximately 15 gallons per acre at 40 pounds per square inch (gauge) spray pressure, with a 20-inch nozzle spacing, at the indicated ground speeds: 8001VS (2 mph), 80015VS (3 mph), 8002VS (4 mph), 8003VS (5 mph). (Spraying Systems Co., Wheaton, Ill.) To optimize the spray pattern, the nozzle height above the target (either the top of the plant canopy or the soil) should be adjusted so that the spray pattern from each nozzle overlaps the spray pattern from each adjacent spray nozzle by about 30% (as measured linearly). Using the 80 degree nozzles listed above, at a 40 psi spraying pressure, and a 20 inch spacing between nozzles, the correct spray height above the target would be 17 to 19 inches. Holding other parameters constant, but changing the nozzle spacing to 30 inches, the correct spray height would increase to 26 to 28 inches. Using spray pressures lower than 40 psi will typically reduce the nozzle spray angles, and adjusting to a lower spray height may be necessary to achieve proper overlap at lower pressures. All spray equipment should be precisely calibrated before use.

When spraying, carefully measured marking flags to guide the spray-rig operator are frequently beneficial, as are flags at midfield in larger fields, in addition to those at the ends the fields. Wind speed should be essentially zero, a condition that is often seen in the early morning or late afternoon. Spraying should not be performed if rain is anticipated within about the next six hours (a time that varies, depending on the particular herbicide). Pre-emergence spraying should be applied to dry ground. If the herbicide requires moisture for activation, then irrigation or rainfall after planting is required.

Uniformity of spraying is best accomplished by dividing the herbicide to be applied equally between two consecutive sprayings, one after the other. The spray solution is prepared at half the final treatment concentration. Two passes are then made in opposite directions to achieve the desired total treatment concentration. For example, if the first pass on a particular row is made in the North-to-South direction, the second pass is made in the South-to-North direction. When spraying with a tractor, this may be accomplished by traveling in the opposite direction in the same tracks for the second application.

Complete coverage is promoted by using large spray volumes (i.e., dilute concentrations of herbicide) and small spray droplet size. Spray volumes of 30 to 40 gallons per acre have worked well, particularly with two applications of 15 to 20 gallons per acre each. Spray pressures of 30 to 40 pounds per square inch (gauge) have worked well in producing fine sprays that provide thorough coverage. Nozzles should be evenly spaced, preferably about 20 inches apart.

The total rate of herbicide application used for the selection is preferably at least twice the normal use rate for that herbicide. For example, if 0.063 lb ai/A is the normal use rate for crops, then an appropriate concentration to select for resistant individuals would be two applications at the same rate, resulting in 0.125 lbs ai/A total treatment.

The combination of two sprayings, large spray volumes, high spray pressures, and an elevated treatment concentration helps minimize the occurrence of escapes, i.e., individuals that are not truly resistant, but that survived the procedure simply because they were inadequately sprayed.

There are advantages to conducting selection with herbicides that possess both soil and foliar activities. The soil activity of the herbicide can be used directly to select for resistant individuals that grow despite the pre-emergence application. Alternatively, a pre-emergence application can be used to eliminate a large percentage of the non-resistant entities, following which a foliar application is made to the surviving individuals. This early thinning of the stand density greatly reduces the problem of spray interception that can otherwise occur within a thick stand of young seedlings, i.e., the possibility of a seedling that is physically shielded from the spray by other seedlings.

Using both soil and foliar application of a suitable herbicide also reduces the problem of "escapes," because the herbicide's soil activity will often eliminate individuals that escape the foliar spray. When using a herbicide having primarily, or only, foliar activity, an additional spraying may be necessary for two reasons. One reason is to eliminate non-resistant individuals that escaped the foliar spray. Also important is the elimination of non-resistant individuals originating from late-sprouting seed. A plant that grows from a seed that sprouts after spraying will not be controlled by a herbicide having only foliar activity. Within two weeks, such a plant may reach a size that makes it appear to be a resistant mutant that survived the foliar treatment. If a second foliar spraying is either undesirable or not possible, an alternative is to leave a small area of the field unsprayed when applying the first application, to provide a direct standard for determining the size that resistant seedlings should achieve during the intervening period.

Using a herbicide with both soil and foliar activity also presents the opportunity to select efficiently for both pre-emergence and post-emergence resistance within the same individual. This selection is accomplished by applying sequential applications. The likelihood is high that individuals surviving sequential applications are resistant to both pre and post-emergence treatments with that herbicide.

As the selection procedure is in progress, care should be taken that the few surviving individuals are not eaten by birds or insects. This is particularly important when using post-emergence treatments, but is also important with pre-emergence treatments. Sound-making devices may be used to drive away birds such as blackbirds, which consume rice seeds and small seedlings. Insects such as fall armyworms and rice water weevils also may kill small survivors, and the application of an insecticide on a preventative basis is frequently desirable. Daily monitoring of the situation should be undertaken if an investigator chooses not to use bird-discouraging devices or insecticides preventatively.

Miscellaneous

Through routine breeding practices known in the art, progeny will be bred from each of the resistant parent lines identified above. Once progeny are identified that are demonstrably resistant, those progeny will be used to breed varieties for commercial use. Crossing and back-crossing the resistant rice with other rice germplasm through standard means will yield herbicide-resistant rice varieties and hybrids having good productivity and other agronomically desirable properties.

Because red rice and commercial rice belong to the same species, the planting of a herbicide-resistant commercial rice crop entails some risk that herbicide resistance would be transferred to red rice. However, rice is self-pollinating, and the frequency of outcrossing is low, even between immediately adjacent plants flowering in synchrony. The likelihood of transferring resistance to red rice could be minimized by breeding resistant varieties that flower significantly earlier than does red rice (e.g., using conventional breeding techniques, or by tissue culture such as anther culture). Maintaining an early-maturing phenotype in resistant varieties, for example, will be desirable to reduce the likelihood of outcrossing to red rice. In addition, breeding higher levels of resistance (e.g., by crossing lines with different AHAS isozymes with one another, or crossing lines with resistant AHAS enzymes with the metabolic resistance of ATCC 75295) will allow control of the outcrossed red rice by applying higher herbicide rates than the outcrossed red rice will tolerate.

If a strain of red rice should nevertheless develop that is resistant to the same herbicides as the resistant commercial rice, the plants can always be treated with a broad range of other available herbicides—particularly if the resistant red rice were discovered early, before having much opportunity to propagate.

Because each of the herbicides tested inhibits the activity of acetohydroxyacid synthase, and because resistance to each of these herbicides has been demonstrated in the novel lines, it is expected that the novel herbicide resistant rice will show resistance to other herbicides that normally inhibit this enzyme. In addition to those discussed above, such herbicides include others of the imidazolinone and sulfonylurea classes, including at least the following: primisulfuron, chlorsulfuron, imazamethabenz methyl, and triasulfuron. Other classes of AHAS herbicides known in the art include triazolopyrimidines, sulfamoylureas, sulfonylcarboxamides, sulfonamides, pyrimidyloxybenzoates, phthalides, pyrimidylsalicylates, carbamoylpyrazolines, sulfonylimino-triazinyl heteroazoles, N-protected valylanilides, sulfonylamide azines, pyrimidyl maleic acids, benzenesulfonyl carboxamides, substituted sulfonyldiamides, and ubiquinone-o.

As used in the specification and claims, the term "mutation-inducing conditions" refers to conditions that will cause mutations in a plant's genome at rates substantially higher than the background rate. A variety of such conditions are well-known to those in the art. They include, for example, exposing seeds to chemical mutagens or ionizing radiation as described above. Such conditions also include growing cells in tissue culture (anther culture, callus culture, suspension culture, protoplast culture, etc.), with or without deliberately exposing the cells to additional mutation-inducing conditions other than those that are inherent in tissue culture. (It is known that tissue culture is per seconducive to the production of genetic variability, including mutations.) Depending on the particular mutation-inducing conditions used, mutations may best be induced at different stages in the life cycle, e.g., with dry seeds, with pre-germinated seeds, etc.

As used in the specification and claims, the term "imidazolinone" means a herbicidal composition comprising one or more chemical compounds of the imidazolinone class, including by way of example and not limitation, 2-(2-imidazolin-2-yl)pyridines, 2-(2-imidazolin-2-yl)quinolines and 2-(2-imidazolin-2-yl) benzoates or derivatives thereof, including their optical isomers, diastereomers and/or tautomers exhibiting herbicidal activity, including by way of example and not limitation 2-[4,5-dihydro-4-methyl-4-(1-methylethyl)-5-oxo-1H-imidazol-2-yl]-3-quinolinecarboxylic acid (generic name imazaquin); 2-[4,5-dihydro-4-methyl-4-(1-methylethyl)-5-oxo-1H-imidazol-2-yl]-5-ethyl-3-pyridinecarboxylic acid (generic name imazethapyr); and 2-[4,5-dihydro-4-methyl-4-(1-methylethyl)-5-oxo-1H-imidazol-2-yl]-5-(methoxymethyl)-3-pyridinecarboxylic acid (generic name imazamox); 2-[4,5-dihydro-4-methyl-4-(1-methylethyl)-5-oxo-1H-imidazol-2-yl]-3-pyridinecarboxylic acid (generic name imazapyr); 2-[4,5-dihydro-4-methyl-4-(1-methylethyl)-5-oxo-1H-imidazol-2-yl]-5-methyl-3-pyridinecarboxylic acid) (generic name imazameth, also known as imazapic); and the other examples of imidazolinone herbicides given in the specification.

As used in the specification and claims, the term "sulfonylurea" means a herbicidal composition comprising one or more chemical compounds of the sulfonylurea class, which generally comprise a sulfonylurea bridge, —$SO_2NHCONH$—, linking two aromatic or heteroaromatic rings, including by way of example and not limitation 2-(((((4,6-dimethoxypyrimidin-2-yl)aminocarbonyl))aminosulfonyl))-N,N-dimethyl-3-pyridinecarboxamide (generic name nicosulfuron); 3-[4,6-bis(difluoromethoxy)-pyrimidin-2-yl]-1-(2-methoxycarbonylphenylsulfonyl)urea (generic name primisulfuron); 2-[[[[(4,6-dimethyl-2-pyrimidinyl)amino]carbonyl]amino]sulfonyl]benzoic acid methyl ester (generic name sulfometuron methyl); methyl 2-[[[[(4-methoxy-6-methyl-1,3,5-triazin-2-yl)amino]carbonyl]amino]sulfonyl]benzoate (generic name metsulfuron methyl); methyl-2-[[[[N-(4-methoxy-6-methyl-1,3,5-triazin-2-yl) methylamino]carbonyl]amino]sulfonyl]benzoate (generic name tribenuron methyl); methyl-3-[[[[(4-methoxy-6-methyl-1,3,5-triazin-2-yl)amino]carbonyl]amino]sulfonyl]-2-thiophenecarboxylate (generic name thifensulfuron methyl); 2-chloro-N-[(4-methoxy-6-methyl-1,3,5-triazin-2-yl)aminocarbonyl]benzenesulfonamide (generic name chlorsulfuron); ethyl 2-[[[[(4-chloro-6-methoxypyrimidin-2-yl) amino]carbonyl]amino]sulfonyl benzoate (generic name chlorimuron ethyl); methyl 2-[[[[N-(4-methoxy-6-methyl-1,3,5-triazin-2-yl)methylamino]carbonyl]amino]sulfonyl benzoate (generic name tribenuron methyl); 3-(6-methoxy-4-methyl-1,3,5-triazin-2-yl)-1-[2-(2-chloroethoxy)-phenylsulfonyl]-urea (generic name triasulfuron); and the other examples of sulfonylurea herbicides given in the specification.

As used in the specification and claims, unless otherwise clearly indicated by context, the term "plant" is intended to encompass plants at any stage of maturity, as well as any cells, tissues, or organs taken or derived from any such plant, including without limitation any seeds, leaves, stems, flowers, fruits, roots, tubers, single cells, gametes, anther cultures, callus cultures, suspension cultures, other tissue cultures, or protoplasts.

Unless otherwise clearly indicated by context, the "progeny" of a plant includes a plant of any subsequent generation whose ancestry can be traced to that plant.

Unless otherwise clearly indicated by context, a "derivative" of a herbicide-resistant plant includes both the progeny of that herbicide-resistant plant, as the term "progeny" is defined above; and also any mutant, recombinant, or genetically-engineered derivative of that plant, whether of the same species or of a different species; where, in either case, the herbicide-resistance characteristics of the original herbicide-resistant plant have been transferred to the derivative plant. Thus a "derivative" of a rice plant with a resistant AHAS enzyme would include, by way of example and not limitation, any of the following plants that express the same resistant AHAS enzyme: $F_1$ progeny rice plants, $F_2$ progeny rice plants, and $F_{30}$ progeny rice plants.

The following definitions should be understood to apply throughout the specification and claims. A "functional" or "normal" AHAS enzyme is one that is capable of catalyzing the first step in the pathway for synthesis of the essential amino acids isoleucine, leucine, and valine. A "wild-type" AHAS enzyme or "wild-type" AHAS sequence is an AHAS enzyme or a DNA sequence encoding an AHAS enzyme, respectively, that is present in a herbicide-sensitive member of a given species. A "resistant" plant is one that produces a functional AHAS enzyme, and that is capable of reaching maturity when grown in the presence of normally inhibitory levels of a herbicide that normally inhibits AHAS. The term "resistant" or "resistance," as used herein, is also intended to encompass "tolerant" plants, i.e., those plants that phenotypically evidence adverse, but not lethal, reactions to one or more AHAS herbicides. A "resistant" AHAS enzyme is a functional AHAS enzyme that retains substantially greater activity than does a wild-type AHAS enzyme in the presence of normally inhibitory levels of an AHAS herbicide, as measured by in vitro assays of the respective enzymes' activities. A "wild-type" or "sensitive" plant is one that produces a functional AHAS enzyme, and that is sensitive to normally inhibitory levels of a herbicide that normally inhibits AHAS. Note that within the contemplation of this last definition, "wild-type" plants include cultivated varieties; the designation "wild-type" refers to the presence or absence of normal levels of herbicide sensitivity, and in the context of this specification and the claims the term "wild-type" carries no connotation as to whether a particular plant is the product of cultivation and artificial selection, or is found in nature in an uncultivated state.

The complete disclosures of all references cited in this specification are hereby incorporated by reference, as is the complete disclosure of U.S. provisional patent application Ser. No. 60/107,255, filed Nov. 5, 1998. In the event of an otherwise irreconcilable conflict, however, the present specification shall control.

Notes on herbicide nomenclature—the following listing gives trade names, generic names, and chemical names for various herbicides: Pursuit™ (imazethapyr: (±)-2-[4,5-dihydro-4-methyl-4-(1-methylethyl)-5-oxo-1H-imidazol-2-yl]-5-ethyl-3-pyridinecarboxylic acid); Scepter™ (imazaquin: 2-[4,5-dihydro-4-methyl-4-(1-methylethyl)-5-oxo-1H-imidazol-2-yl]-3-quinolinecarboxylic acid); Accent™ (nicosulfuron: 2-(((((4,6-dimethoxypyrimidin-2-yl)aminocarbonyl)) aminosulfonyl))-N,N-dimethyl-3-pyridinecarboxamide); Beacon™ (primisulfuron: 3-[4,6-bis(difluoromethoxy)-pyrimidin-2-yl]-1-(2-methoxycarbonylphenylsulfonyl)urea); Raptor™ (imazamox: (+)-5-methoxymethyl-2-(4-isopropyl-4-methyl-5-oxo-2-imidazolin-2-yl) nicotinic acid; Cadre™ (imazapic: (±)-2-[4,5-dihydro-4-methyl-4-(1-methyl-ethyl)-5-oxo-1H-imidazol-2-yl]-5-methyl-3-pyridinecarboxylic acid; alternate chemical name (±)-2-(4-isopropyl-4-methyl-5-oxo-2-imidazolin-2-yl)-5-methylnicotinic acid); Arsenal™ (imazapyr: 2-[4,5-dihydro-4-methyl-4-(1-methyl-ethyl)-5-oxo-1H-imidazol-2-yl]-3-pyridinecarboxylic acid); Oust™ (sulfometuron methyl: chemical name 2-[[[[(4,6-dimethyl-2-pyrimidinyl)amino]carbonyl]amino]sulfonyl] benzoic acid methyl ester); Ally™ (metsulfuron methyl: methyl 2-[[[[(4-methoxy-6-methyl-1,3,5-triazin-2-yl) amino]carbonyl]amino]sulfonyl]benzoate); Harmony™ (mixture of thifensulfuron methyl and tribenuron methyl: mixture of methyl-3-[[[[(4-methoxy-6-methyl-1,3,5-triazin-2-yl)amino]carbonyl]amino]sulfonyl]-2-thiophenecarboxylate and methyl-2-[[[[N-(4-methoxy-6-methyl-1,3,5-triazin-2-yl)methylamino]carbonyl]amino]sulfonyl]benzoate); Pinnacle™ (thifensulfuron methyl: methyl-3-[[[[(4-methoxy-6-methyl-1,3,5-triazin-2-yl)amino]carbonyl]amino]sulfonyl]-2-thiophenecarboxylate); Glean™ or Telar™ (chlorsulfuron: 2-chloro-N-[(4-methoxy-6-methyl-1,3,5-triazin-2-yl)aminocarbonyl]benzenesulfonamide); Classic™ (chlorimuron ethyl: ethyl 2-[[[[(4-chloro-6-methoxypyrimidin-2-yl)amino]carbonyl]amino]sulfonyl benzoate); Express™ (tribenuron methyl: methyl 2-[[[[N-(4-methoxy-6-methyl-1,3,5-triazin-2-yl)methylamino]carbonyl]amino] sulfonyl benzoate); Assert™ (imazamethabenz methyl: m-toluic acid, 6-(4-isopropyl-4-methyl-5-oxo-2-imidazolin-2-yl)-, methyl ester; and p-toluic acid, 2-(4-isopropyl-4-methyl-5-oxo-2-imidazolin-2-yl)-, methyl ester); and Amber™ (triasulfuron: 3-(6-methoxy-4-methyl-1,3,5-triazin-2-yl)-1-[2-(2-chloroethoxy)-phenylsulfonyl]-urea); Staple™ (pyrithiobac sodium: sodium 2-chloro-6-[(4,6-dimethoxy pyrimidin-2-yl)thio]benzoate); and Matrix™ (rimsulfuron: N-((4,6-dimethoxypyrimidin-2-yl)aminocarbonyl)-3-(ethylsulfonyl)-2-pyridinesulfonamide).

What is claimed:

1. An imidazolinone herbicide-resistant rice plant of any one of the lines PWC16, PWC23, CMC29, and WDC38, representative samples of seed of these lines having been deposited, respectively, under ATCC accession numbers PTA-904, PTA-905, PTA-902, and PTA-908.

2. A seed of or capable of producing the plant of claim 1.

3. A plant cell of the plant of claim 1.

4. A plant product prepared from the plant of claim 1.

5. The plant product of claim 4, wherein said plant product is a seed.

6. A method for controlling weeds in the vicinity of the plant of claim 1, said method comprising applying a herbicide to the weeds and to the plant, at a level of the herbicide that would normally inhibit the growth of a wild-type rice plant.

7. The method of claim 6, wherein said step of applying comprises applying the herbicide at a pre-emergence stage, a post-emergence stage, or both.

8. The method of claim 6, wherein the herbicide that is applied to the weeds and to the plant comprises a herbicidally-effective imidazolinone.

9. The method of claim 8, wherein the herbicide that is applied to the weeds and to the plant comprises imazethapyr.

10. The method of claim 8, wherein the herbicide that is applied to the weeds and to the plant comprises imazapic.

11. The method of claim 8, wherein the herbicide that is applied to the weeds and to the plant comprises imazaquin.

12. The method of claim 8, wherein the herbicide that is applied to the weeds and to the plant comprises imazamox.

13. The method of claim 8, wherein the herbicide that is applied to the weeds and to the plant comprises imazapyr.

14. The method of claim 6, wherein the herbicide that is applied to the weeds and to the plant comprises a herbicidally-effective sulfonylurea.

15. The method of claim 14, wherein the herbicide that is applied to the weeds and to the plant comprises nicosulfuron.

16. The method of claim 14, wherein the herbicide that is applied to the weeds and to the plant comprises metsulfuron methyl.

17. The method of claim 14, wherein the herbicide that is applied to the weeds and to the plant comprises thifensulfuron methyl.

18. The method of claim 14, wherein the herbicide that is applied to the weeds and to the plant comprises tribenuron methyl.

19. The method of claim 14, wherein the herbicide that is applied to the weeds and to the plant comprises pyrithiobac sodium.

20. A method for producing a herbicide-tolerant plant, said method comprising crossing or back-crossing the plant of claim 1 with other germplasm to produce a herbicide-tolerant plant.

21. A plant produced by the method of claim 20; or a seed, plant cell, or plant product thereof.

22. The seed of claim 2, wherein said seed is a seed of line PWC16.

23. The seed of claim 2, wherein said seed is a seed of line PWC23.

24. The seed of claim 2, wherein said seed is a seed of line CMC29.

25. The seed of claim 2, wherein said seed is a seed of line WDC38.

26. An $F_1$ progeny of the plant of claim 1, wherein said $F_1$ progeny is resistant to one or more imidazolinone herbicides;

and wherein said $F_1$ progeny further expresses tolerance to nicosulfuron; and wherein said $F_1$ progeny expresses a mutant acetohydroxyacid synthase that is directly resistant to levels of herbicide that normally inhibit wild-type acetohydroxyacid synthase.

27. A method for controlling weeds in the vicinity of the $F_1$ progeny of claim 26, said method comprising applying a herbicide to the weeds and to said $F_1$ progeny, at a level of the herbicide that would normally inhibit the growth of a wild-type rice plant.

28. The method of claim 27, additionally comprising the step of harvesting seed produced by said $F_1$ progeny.

* * * * *

UNITED STATES PATENT AND TRADEMARK OFFICE
CERTIFICATE OF CORRECTION

Page 1 of 2

PATENT NO. : 9,029,642 B2
APPLICATION NO. : 12/819360
DATED : May 12, 2015
INVENTOR(S) : Timothy P. Croughan It is certified that error appears in the above-identified patent and that said Letters Patent is hereby corrected as shown below:

In the Specification

Col. 9, line 44, after "only" delete the "."

Col. 16, Table 3, in the heading for the rightmost column:

replace
```
Imazapic
 0.05 +
Imazapyr 0.05
post
```
with
```
Imazapic 0.05 +
 Imazapyr 0.05 post
```

Col. 17, Table 3, in the heading for the second column:

replace
```
Imazapic 0.075 +

Imazapyr 0.025
post
```
with
```
Imazapic 0.075 +
 Imazapyr 0.025 post
```

Signed and Sealed this
First Day of March, 2016

Michelle K. Lee
*Director of the United States Patent and Trademark Office*

CERTIFICATE OF CORRECTION (continued)
U.S. Pat. No. 9,029,642 B2

In the Specification

Col. 18, Table 3, in the heading for the third column:

*replace*

| Imazapic 0.015 +   |
|                    |
| Imazapyr 0.05      |
| post               |

*with*

| Imazapic 0.015 +   |
| Imazapyr 0.05      |
|                    |
| post               |

Col. 21, line 57, replace "another" with – anther –

Col. 23, line 24, after "ends" insert -- of --

Col. 25, line 38, replace "per seconducive" with – *per se* conducive –